(12) United States Patent
Batiste et al.

(10) Patent No.: US 8,900,177 B2
(45) Date of Patent: Dec. 2, 2014

(54) SELF ADJUSTING VENOUS EQUALIZING GRAFT

(76) Inventors: Stanley Batiste, Granite Bay, CA (US); Steven Achstein, Roseville, CA (US)

( * ) Notice: Subject to any disclaimer, the term of this patent is extended or adjusted under 35 U.S.C. 154(b) by 994 days.

(21) Appl. No.: 12/723,032

(22) Filed: Mar. 12, 2010

(65) Prior Publication Data

US 2010/0234789 A1 Sep. 16, 2010

Related U.S. Application Data

(60) Provisional application No. 61/210,016, filed on Mar. 13, 2009.

(51) Int. Cl.
*A61M 5/00* (2006.01)
*A61M 1/36* (2006.01)

(52) U.S. Cl.
CPC ........... *A61M 1/3653* (2013.01); *A61M 1/3655* (2013.01)
USPC .................................................. 604/8; 604/9

(58) Field of Classification Search
CPC ............ A61M 27/008; A61M 27/006; A61M 27/002; A61M 1/3653; A61M 1/3655; A61F 2/04
USPC ......................................................... 604/8, 9
See application file for complete search history.

(56) References Cited

U.S. PATENT DOCUMENTS

| | | | |
|---|---|---|---|
| 3,826,257 A | 7/1974 | Buselmeier | |
| 4,549,879 A | 10/1985 | Groshong et al. | |
| 4,552,552 A * | 11/1985 | Polaschegg et al. | 604/6.05 |
| 4,753,640 A | 6/1988 | Nichols et al. | |
| 5,713,859 A | 2/1998 | Finch, Jr. et al. | |
| 5,800,514 A | 9/1998 | Nunez et al. | |
| 5,849,036 A | 12/1998 | Zarate | |
| 6,056,717 A | 5/2000 | Finch et al. | |
| 6,146,414 A | 11/2000 | Gelman | |
| 6,338,724 B1 | 1/2002 | Dossa | |
| 6,371,981 B1 | 4/2002 | Yang et al. | |
| 6,461,321 B1 | 10/2002 | Quinn | |
| 6,544,208 B2 * | 4/2003 | Ethier et al. | 604/8 |
| 6,585,762 B1 | 7/2003 | Stanish | |
| 6,598,278 B2 | 7/2003 | Chen et al. | |
| 7,025,741 B2 | 4/2006 | Cull | |
| 7,108,673 B1 * | 9/2006 | Batiste | 604/6.16 |
| 7,192,413 B2 * | 3/2007 | Kraus et al. | 604/9 |
| 7,435,059 B2 * | 10/2008 | Smith et al. | 417/26 |

(Continued)

FOREIGN PATENT DOCUMENTS

WO  WO 2009/152488  6/2009

*Primary Examiner* — Philip R Wiest
*Assistant Examiner* — Ariana Zimbouski
(74) *Attorney, Agent, or Firm* — Weide & Miller, Ltd.

(57) ABSTRACT

A self adjusting venous equalizing graft (SAVE graft) which provides a self regulating stenosis is provided herein. The SAVE graft responds to increases or decreases in blood pressure which allows a higher pressure at the graft's arterial end and a lower pressure at the graft's venous end. This is ideal in that it mimics the natural pressure of a patient's circulatory system. A dialysis machine may draw blood at the arterial end, dialyze the blood, and return the blood to the patient at the graft's venous end. The lower pressure at the venous end prevents damage to the patient's vein. The SAVE graft may comprise a deformable stenosis control diaphragm or a venous controlled pressure nozzle which may expand or contract in response to blood pressure to self regulate the stenosis provided by the SAVE graft.

13 Claims, 5 Drawing Sheets

(56) References Cited

U.S. PATENT DOCUMENTS

| | | | |
|---|---|---|---|
| 7,540,859 B2* | 6/2009 | Claude et al. | 604/246 |
| 7,566,317 B1 | 7/2009 | Batiste et al. | |
| 7,832,431 B2* | 11/2010 | Doig | 137/853 |
| 2002/0092536 A1* | 7/2002 | LaFontaine et al. | 128/898 |
| 2005/0038396 A1* | 2/2005 | Claude et al. | 604/246 |
| 2005/0148925 A1* | 7/2005 | Rottenberg et al. | 604/9 |
| 2009/0234431 A1 | 9/2009 | Weinberger et al. | |

* cited by examiner

SELF ADJUSTING VENOUS EQUALIZING GRAFT

CROSS-REFERENCE TO RELATED APPLICATION

This application claims priority to U.S. Provisional Patent Application No. 61/210,016, entitled Self Adjusting Venous Equalizing Graft, filed Mar. 13, 2009.

BACKGROUND OF THE INVENTION

1. Field of the Invention

The invention relates generally to venous grafts and in particular to a self adjusting equalizing graft.

2. Related Art

There are currently more than 400,000 patients in the United States with end-stage renal disease (ESRD) and many times more than that throughout the world. ESRD accounts for approximately 6.4% of the overall Medicare budget at over $23 billion dollars in the US in 2006. Patients with end stage renal disease have lost their normal kidney function and as a result require dialysis to substitute the function of the kidney cleansing the blood. There are two types of dialysis; hemodialysis and peritoneal dialysis. For purposes of this overview we will primarily be focused on hemodialysis and later discuss briefly the topic of peritoneal dialysis.

Hemodialysis requires that large volume blood access and exchange be consistently available to sustain the life of the patient. Typically, a dialysis patient will require 3-4 hours of dialysis three days a week. The challenge with providing hemodialysis is maintaining access to large volumes of blood when a body constantly fights attempts to keep access available by healing closed such access. Currently there are three ways to provide hemodialysis; dialysis catheters, arterial venous fistulas (AVF's) and arterial venous grafts (AVGs). Although used world wide, catheters are known not to be efficient for long term dialysis. Unfortunately, catheters have very short patency rates and high rates of infection. For these reasons dialysis guidelines strongly oppose catheter use, other than short term, until fistula or graft placement is available.

AVG's and AVF's are synthetic and natural conduits respectively that are surgically placed to provide long term dialysis access. Both provide large diameter targets that can be easily accessed with large needles for blood exchange. These conduits are commonly placed in the arm with the furthest point attached to the patient's artery and then are directly attached to the vein for blood flow return. The high arterial blood pressure and flow is shunted directly to the vein providing dilatation of the vein or graft and large volume blood flow. Although these methods provide excellent means of access both have limitations with regard to sustaining long term patency. The patency rates are much greater than that of a catheter however overall are relatively poor when considering the few years gained in a patient's life. It has been noted that there is only 50% shunt patency at one year and less than 25% at 2 years. Not only does this create a huge burden on the cost of healthcare but more importantly, once access is no longer available, a new access point must be created to sustain a patient's life.

A thorough description of the reason for dialysis fistula and graft failure is beyond the scope of this document. The fundamental problem is that the flow dynamics created by these artificial conduits are not normal to our bodies. The change is detected by the body and the normal physiologic defenses become involved and attempt to return the system to normal.

From the discussion that follows, it will become apparent that the present invention addresses the deficiencies associated with the prior art while providing numerous additional advantages and benefits not contemplated or possible with prior art constructions.

SUMMARY OF THE INVENTION

A SAVE (self adjusting venous equalizing) graft is provided herein. The SAVE graft provides a stenosis which creates an increased pressure at an inflow end of the graft and a decreased pressure at an outflow end of the graft. In this manner, blood may be drawn from the increased pressure blood flow at the inflow end and returned to a patient at the outflow end at a decreased pressure which is natural or native to the veins of a patient's circulatory system. In general, the decreased venous pressure extends the life of a graft by preventing scarring of the veins. The increased pressure at the inflow end prevents the dangerous "stealing" of blood flow to parts of a patient's body downstream from the graft. The SAVE graft provides a self regulating stenosis which may increase or decrease in stenosis size based on the patient's venous blood pressure, arterial blood pressure, or both. The SAVE graft does not require operator intervention to adjust its stenosis.

The SAVE graft may have a variety of configurations. For example, in one embodiment the graft may be a self adjusting graft comprising an inflow end for accepting a blood flow from a circulatory system, and an outflow end for returning the blood flow at an outflow pressure to the circulatory system. A conduit within the self adjusting graft may be configured to provide a fluid pathway for the blood flow between the inflow end and the outflow end. An internal reservoir between the inflow end and the outflow end and having a reservoir pressure may be included. The internal reservoir may be formed by an outer wall of the self adjusting graft and the conduit. A collapsible portion of the conduit configured to provide a stenosis for the blood flow may also be included. The outflow pressure increasing relative to the reservoir pressure collapses the collapsible portion and the outflow pressure decreasing relative to the reservoir pressure returns the collapsible portion to a substantially uncollapsed state.

It is noted that the collapsible portion may have a cylindrical shape. In addition, the inflow end may be configured to attach to an artery of the circulatory system and the outflow end may be configured to attach to a vein of the circulatory system. A puncture prevention covering surrounding at least a portion of the outer wall may also be provided.

The conduit may comprise an expandable portion between the collapsible portion and the outflow end. The expandable portion may be configured to pressurize the internal reservoir by expanding into the internal reservoir as outflow pressure increases. In addition, the conduit may comprise a tapered portion between the inflow end and the collapsible portion, the tapered portion configured to direct pressure within the internal reservoir to the collapsible portion to thereby collapse the collapsible portion.

The conduit may also or alternatively comprise a tapered portion between the inflow end and the collapsible portion and an expandable portion between the collapsible portion and the outflow end. The expandable portion may be configured to pressurize the internal reservoir by expanding into the internal reservoir as blood pressure at the outflow end increases, and the tapered portion may be configured to direct pressure within the internal reservoir on the collapsible portion to thereby collapse the collapsible portion.

In another exemplary embodiment, a self adjusting graft may comprise an inflow end for accepting a blood flow from a circulatory system, an outflow end for returning the blood flow to the circulatory system, and a conduit within the self adjusting graft configured to provide a fluid pathway for the blood flow between the inflow end and the outflow end.

A collapsible portion of the conduit may be included to provide a stenosis for the blood flow such that an increase in blood pressure at the outflow end collapses the collapsible portion and a decrease in blood pressure returns the collapsible portion to a substantially uncollapsed state. A tapered portion of the conduit may be configured to form a stenosis. The tapered portion may taper in various directions, such as towards the collapsible portion.

Various self adjusting stenosis for a graft are also disclosed. In one embodiment, the self adjusting stenosis may comprise a blood flow conduit located within the graft and configured to provide a fluid pathway for blood flow between an inflow end and an outflow end of the graft. A reservoir may be formed between the blood flow conduit and an outer wall of the graft. The blood flow conduit may have various portions. For example, a collapsible portion of the blood flow conduit may be configured to decrease the blood flow through the blood flow conduit by collapsing as a result of an increase in pressure within the reservoir, and an expandable portion of the blood flow conduit may be configured to pressurize the reservoir by expanding into the reservoir as a result of increased blood pressure at the outflow end of the graft.

The expandable portion may be between the collapsible portion and the outflow end of the graft. Also, the expandable portion may taper outward from the collapsible portion. Similar to above, the collapsible portion may be cylindrical in shape. It is noted that the blood flow conduit may have a tapered portion configured to direct pressure from the reservoir to the collapsible portion to collapse the collapsible portion. The tapered portion may taper inward toward the collapsible portion. A reinforcing covering may surround at least a portion of the outer wall of the graft. The reinforcing covering may be configured to prevent pressurization of the reservoir from expanding the outer wall of the graft outward.

Various methods of controlling stenosis through a graft are also disclosed herein. In one embodiment, the method may comprise accepting a blood flow via a first end of a blood flow conduit within the graft (where the blood flow conduit provides a fluid pathway within the graft for the blood flow), providing a collapsible portion of the blood flow conduit to form a stenosis, and providing a pressure reservoir between an outer wall of the graft and the blood flow conduit. The blood flow may be returned to a circulatory system via a second end of the blood flow conduit.

An expandable portion of the blood flow conduit may expand as a result of increased blood pressure at the second end of the blood flow conduit. The expandable portion may expand into the pressure reservoir. The collapsible portion may collapse as a result of increased pressure within the pressure reservoir. Collapsing the collapsible portion narrows the stenosis. It is noted that pressure within the pressure reservoir may be directed toward the collapsible portion with a tapered portion of the blood flow conduit. The tapered portion may taper in various directions. For example the tapered portion may taper inward toward the collapsible portion.

The method may also comprise returning the expandable portion to a substantially unexpanded state as the blood pressure at the second end of the blood flow conduit is reduced, and/or returning the collapsible portion to a substantially uncollapsed state as a result of decreased pressure within the pressure reservoir. It is noted that an inflow end of the graft may be connected to an artery of the circulatory system and an outflow end of the graft may be connected to a vein of the circulatory system. Also, the rigidity of a portion of the outer wall of the graft may be increased with a reinforcing covering.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION OF THE PREFERRED EMBODIMENTS

Figure 1:
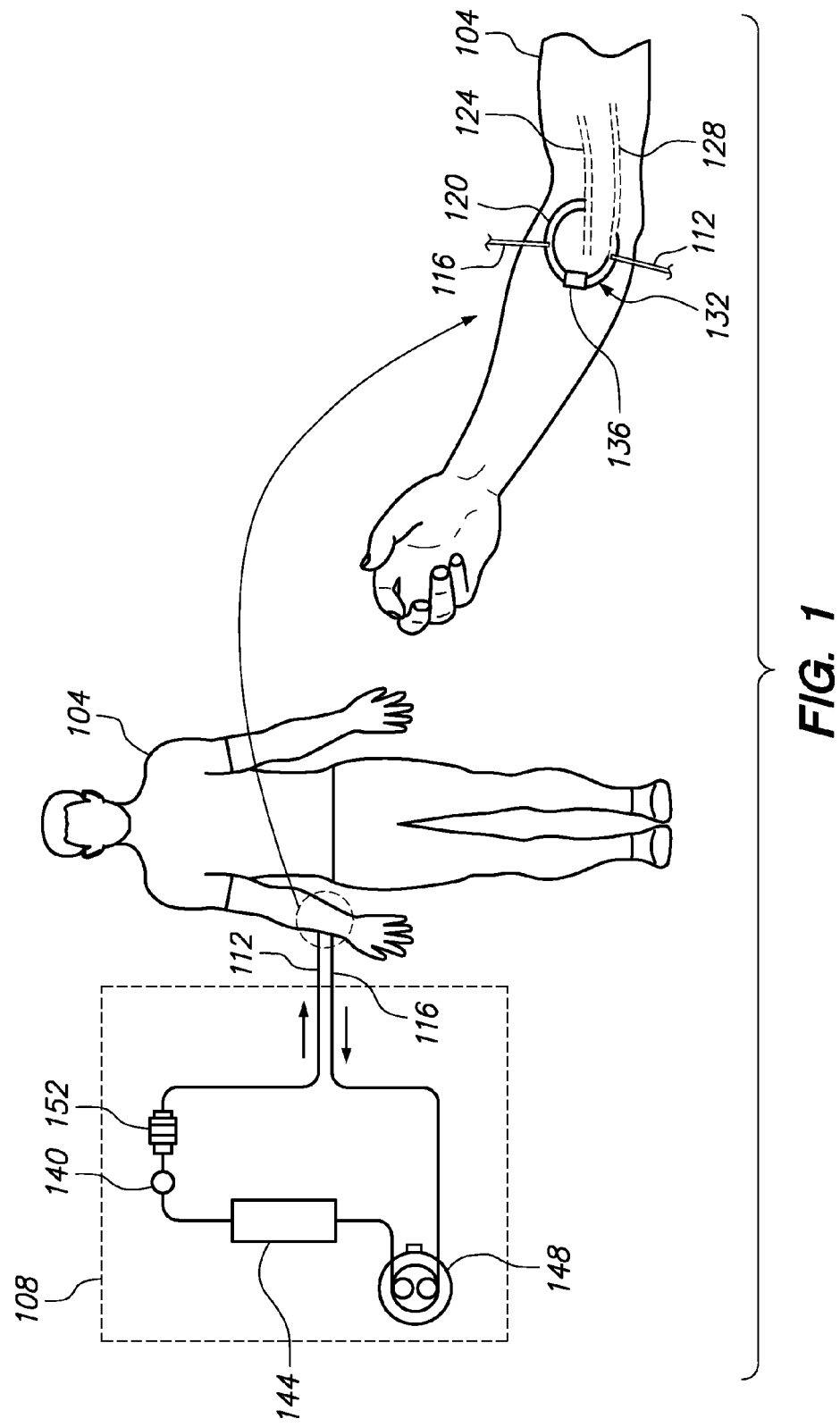
FIG. 1 illustrates a dialysis machine connected to a patient and placement of an exemplary SAVE graft according to an embodiment of the invention.

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

The self adjusting venous equalizing graft (SAVE graft) disclosed herein provides a self regulating stenosis. The stenosis creates a higher pressure blood flow at one end of the graft and a lower pressure flow at the other end of the graft. This provides the benefit of a lower pressure where blood flows from the graft to the vein, while still maintaining a higher pressure on the arterial side of the stenosis and at a point where blood may be drawn to a dialysis machine. The lower pressure more closely matches the natural pressure of the circulatory system while the higher pressure allows blood to be efficiently drawn to a dialysis machine and to serve circulatory needs downstream the artery from the graft. It will be understood that though generally described herein with regard to dialysis and dialysis machines, the SAVE graft may benefit and be used with other circulatory procedures.

The configuration of a stenosis may range from abrupt to smooth tapering or any other shape to create the restriction. Also, a stenosis is generally positioned between both access points or sides of a graft. It is contemplated that the stenosis may be located at any point between the intake and outtake opening. This design maintains high pressure on the arterial end (proximal end) which is the end of the graft for drawing off the patient's blood by the dialysis machine. It is contemplated that the stenosis may be located at any point between the intake and outtake opening.

One advantage of this stenosis is that it creates resistance to blood flow which lowers the pressure of the blood returning from the dialysis machine to the patient. The low pressure nature of the returning flow blood eases the pressure on a patient's vein(s) from blood returning from a dialysis machine. This damping of the pressure and flow rate creates a system like that of normal physiology when the patient is not subject to having a graft. This is important as it has been shown that most grafts fail due to the increased pressure and flow at the point in which the graft connects to a vein. Failure may occur due to a type of intraluminal scarring (intimal hyperplasia) within the veins, slowly closing the veins off at or near the point of graft outflow.

Another advantage is that the SAVE graft's stenosis reduces or eliminates the "stealing" of blood by a dialysis machine or the like. To illustrate, patients have had a continuous high flow/high pressure shunt or graft implanted for dialysis. This type of shunt may cause blood flow to bypass or be reduced to portions of the patient's circulatory system. In this manner, the shunt creates what is called in medicine a "steal", which steals blood from the heart by bypassing the body's tissues and returning blood to the heart unused. This creates undue and continued stress on the heart and can cause a situation where the blood flow to the hand, arm, or other extremities is compromised. In fact, most dialysis related access conflicts arise from grafts which steal blood from the hand, decreasing circulation/perfusion and resulting in loss of fingers.

Traditional grafts may be configured with a fixed stenosis or an operator adjustable stenosis. For example, a stenosis balloon design may be used to provide the stenosis described above in an adjustable manner. The balloon may inflate or deflate to adjust and maintain the stenosis, and hence blood pressure, within a graft. This design generally comprises four main components: a dialysis graft, a central stenosis balloon, an injection reservoir, and a catheter connecting the reservoir to the balloon. These components may be placed surgically and, except for the external control portions, may remain under a patient's skin for the life of the graft. However, the stenosis must be adjusted by a physician or a trained operator. Even then, it is difficult for a physician to determine the best pressure, and because blood pressure is not static, this selected pressure may be non-ideal over the course of a day as the patient is active or sleeping.

In contrast to a fixed stenosis and the operator or physician adjustable stenosis, the SAVE graft uses a stenosis that is self regulating. The self regulating stenosis allows the pressure from the inflow, outflow, or both ends of a graft to adjust the stenosis allowing for optimal venous outflow pressures and flow rates. By using this method there will be no operator error in stenosis adjustment and there will be advantages achieved with improved graft hemodynamics.

The SAVE graft may be configured in various ways that use the graft's internal pressure regulating ability to create the optimum flow dynamics for hemodialysis. Some configurations and details of use are described in detail below. It will become apparent to one skilled in the art from the descriptions herein that elements of the various configurations herein may be combined in different embodiments of the SAVE graft.

FIG. 1 illustrates a patient 104 undergoing dialysis. As shown, a dialysis machine 108 is connected to the patient's forearm by an inflow tube 116 and an outflow tube 112. The exemplary dialysis machine 108 comprises a pump 148, a dialyzer 144, a pressure monitor 140, and an air trap 152 to perform its function. It will be understood that other dialysis machines or other blood processing devices may be used with the SAVE graft. A patient's blood may enter the dialysis machine 108 from the inflow tube 116. Once processed by the dialysis machine 108, the blood may return to the patient 104 via the outflow tube 112.

As shown in FIG. 1, an arterial venous graft (AVG) 120 having a SAVE graft 136 may be located in a patient's 104 forearm or upper arm, or any other location in the body. It is contemplated that the SAVE graft 136 may be utilized as a stand alone graft, or with dialysis, or any other access in intervention procedure. This configuration allows inflow and outflow tubes 116,112 to be connected to the patient's forearm or upper arm. The proximal end of the AVG 120 may be attached to an artery 124 and the distal end may be attached to a vein 128. The pressure differential between the artery 124 and the vein 128 dictates that flow travels thought the AVG 120 from the proximal (i.e. arterial) end towards the distal (i.e. venous) end. For this reason, the inflow tube 116 of a dialysis machine 108 may be connected to the arterial end of the AVG 120 while the outflow tube is connected to the venous end of the AVG.

Figure 2:
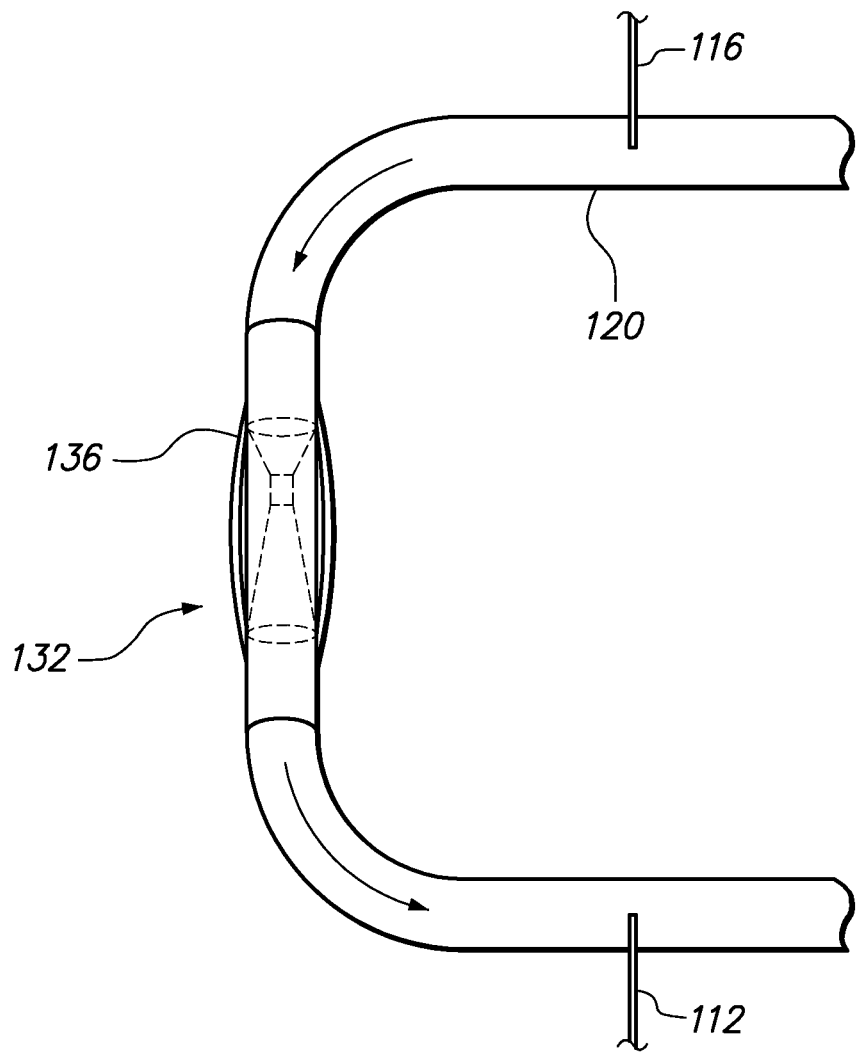
FIG. 2 is a cross section view illustrating an exemplary SAVE graft in place within a graft.

The SAVE graft 136 may be positioned at the apex 132 of the AVG 120 to create resistance to blood flow within the AVG, such as by providing a central stenosis. This ultimately decreases the pressure and return flow to the vein 128. FIG. 2 provides a better view of an exemplary SAVE graft 136 within an AVG 120. As shown, the SAVE graft 136 is positioned generally at the apex of the AVG 120. Of course, it is contemplated that the SAVE graft 136 may be positioned at any locations along or within an AVG 120.

FIG. 2 also illustrates how inflow and outflow conduits may access a patient's blood flow with respect to the SAVE graft 136. As shown, the blood flow, illustrated by the arrows of FIG. 2, is flowing from a proximal (i.e. arterial) end of the SAVE graft 136 towards the distal (i.e. venous) end of the SAVE graft. Access to the blood flow by an inflow tube 116 may be at the arterial end where blood pressure is higher while return of the blood flow by an outflow tube 112 may be at the venous end where pressure is lower to achieve the benefits discussed herein.

Access to the patient's blood flow by the inflow tube 116, outflow tube 112, or both may be through the AVG 120, such as illustrated, or through the SAVE graft 136 itself. For example, the inflow tube 116, outflow tube 112, or both may access blood flow through a portion of the SAVE graft 136. It is contemplated that the inflow tube 116 may access blood flow at the arterial end of the SAVE graft 136 directly through a patient's artery. Likewise, the outflow tube 116 may return blood directly to a patient's vein at the venous end of the SAVE graft 136.

In one or more embodiments, the SAVE graft may have an internal conduit which allows blood to flow through the SAVE graft. The internal conduit may have one or more expandable portions and one or more collapsible portions, as will be described further below. In one or more embodiments, the space or area between the internal conduit and the outer wall of the SAVE graft may form a pressure reservoir. Expansion of the expandable portion into the pressure reservoir causes an increase in pressure within the reservoir. The increased pressure causes the collapsible portion to narrow or collapse thereby narrowing the stenosis of the SAVE graft. As pressure is decreased within the pressure reservoir, the collapsible portion may return to an uncollapsed state widening the stenosis of the SAVE graft.

Figure 3:
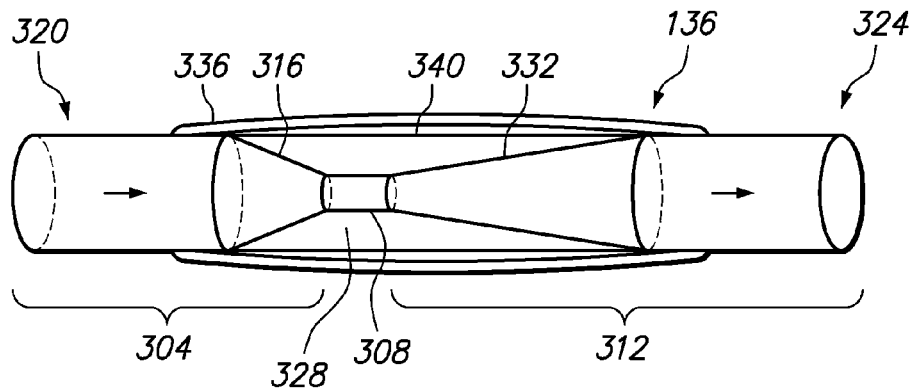
FIG. 3 is a cross section view illustrating an exemplary SAVE graft.

As shown in FIG. 3, the SAVE graft may comprise an internal conduit between an inflow end 320 and an outflow end 324 of the graft which forms a fluid pathway for blood flow through the graft. For example, as shown the internal conduit comprises an arterial pressure control surface (APCS) 316, a stenosis control diaphragm (SCD) 308, and a venous pressure control surface (VPCS) 332. An outer wall 340 may extend the length of the SAVE graft 136 and support various parts of the SAVE graft therein, as described further below. In one embodiment, the ends of the outer wall 340 form an inflow end 320 and an outflow end 324 for blood flow as shown by the arrows of FIG. 3. The outer wall 340 or a portion thereof may be surrounded by a puncture prevention guard (PPG) 336 which protects the SAVE graft 136 from damage, among other things, as will be described further below.

The arterial portion 304, SCD 308, and venous portion 312 will generally be in fluid communication such as shown in FIG. 3. The arterial portion 304 accepts blood flow at an inflow end 320 of the SAVE graft 136. The arterial portion 304 may comprise an arterial pressure control surface 316 which tapers toward the SCD 308. As shown for example, the APCS 316 is tapered conical portion of the arterial portion 304. The APCS 316 may be formed from resilient flexible or stretchable material. The compliance of this material may thus act as a plane to direct force to a pressure reservoir 328, which will be described further below. It is noted that the APCS 316 may also be formed from an inflexible or substantially inflexible material to direct force to the pressure reservoir 328 in one or more embodiments.

The venous portion 312 allows blood to flow out of the SAVE graft 136 at an outflow end 324. The direction of blood flow within the venous portion 312 is illustrated by the arrow therein. The venous portion 312 may comprise a venous pressure control surface 332. In one or more embodiments, the VPCS 332 may be constructed with a smooth conical tapering surface directed away from the SCD 308. The VPCS 332 may also be formed from resilient flexible or stretchable material to allow the VPCS to deform or expand with changes in blood pressure within the venous end 312 of the SAVE graft 136. When venous pressures increases, the deformation or expansion of the VPCS 332 creates increased pressure within the pressure reservoir 328. In this manner, the VPCS 332 forms an expandable portion of the SAVE graft's internal conduit.

In one or more embodiments, the pressure reservoir 328 may be a reservoir formed between the internal conduit and the outer wall 340 of the SAVE graft. For instance, as shown the pressure reservoir 328 may be formed around the APCS 316, the SCD 308, and the VPCS 332 as shown in FIG. 3. As pressure within the pressure reservoir 328 increases, such as caused by the expansion of the VPCS 332 due to increased venous pressure, the SCD 308 (or collapsible portion of the SAVE graft's internal conduit) may be deformed inward or collapse as will be described below. Typically, but not always, the pressure reservoir 328 may be filled with material of low compressibility. The filler transfers force from the expansion of the VPCS 332, the APCS 316, or both to the SCD 308, deforming the SCD inward. It is contemplated that the filler material may be liquid or gaseous in one or more embodiments.

Figure 4A:
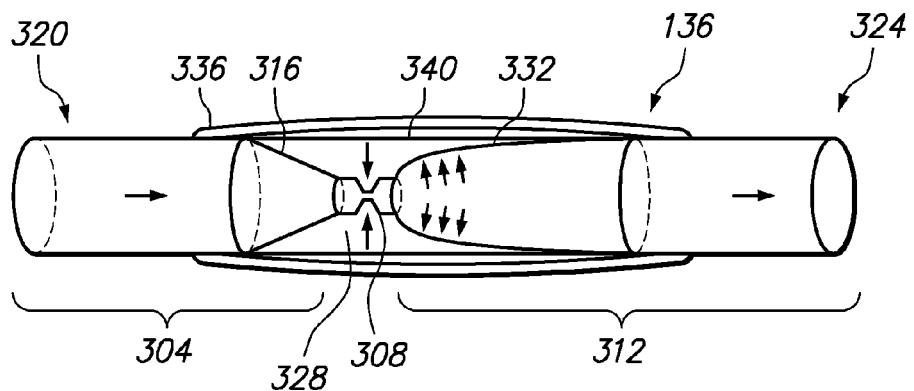
FIG. 4A is a cross section view illustrating an exemplary SAVE graft in an increased pressure state.

FIG. 4A illustrates a SAVE graft in an increased or high venous pressure state. In this state, blood pressure at the outflow end 324 of the SAVE graft is increased or high. As can be seen by the arrows of FIG. 4A, the pressure has caused the VPCS 332 to expand increasing pressure within the pressure reservoir 328. The increased pressure within the pressure reservoir 328 acts upon the SCD 308 deforming it inward, as illustrated by the inward arrows of FIG. 4A. This inward deformity will lead to a circumferential dilatation of the SCD 308 which will narrow the inner lumen of the SAVE graft. This narrows the stenosis provided by the SAVE graft. The narrowed stenosis increases the resistance to blood flow through the arterial and venous ends which decreases the flow rate. The decreased flow rate leads to decreased venous volume and therefore decreased venous pressures.

Figure 4B:
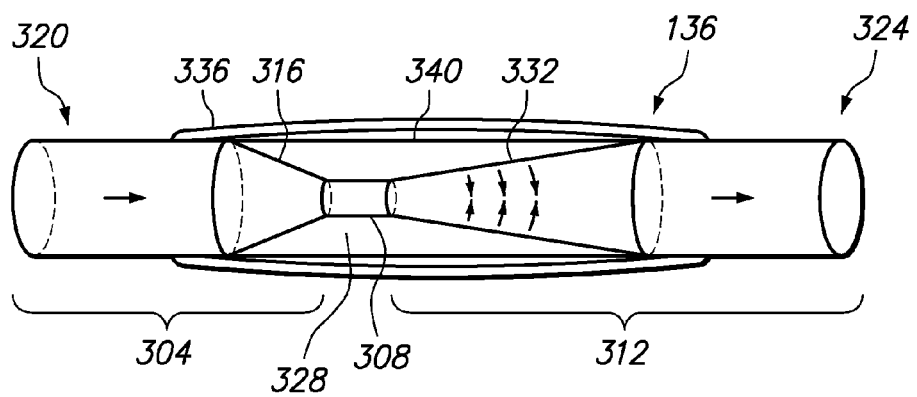
FIG. 4B is a cross section view illustrating an exemplary SAVE graft in a decreased pressure state.

Conversely, as shown in FIG. 4B, as venous pressures decrease, the pressure inside the pressure reservoir 328 will decrease and the SCD 308 will expand outward increasing the luminal diameter of the SAVE graft 136, thus increasing flow through the graft. In turn, pressure at the outflow is increased.

The SCD 308 may be formed from various resilient flexible materials to allow the SCD to collapse or narrow and also return to a substantially or fully uncollapsed state. For example, the SCD 308 may be formed from rubber, plastic, or both. The walls SCD 308 may have thinner sections in one or more embodiments to allow the SCD to better respond to pressure changes within the pressure reservoir 328. In addition, or alternatively, the materials used to form the SCD 308 may be selected for their flexibility. In this manner, the SCD 308 may deform inward the desired amount for a given pressure within the pressure reservoir 328.

It is noted that the VPCS 332, the APCS 316, the SCD 308, or all three may have a different flexibilities, such as by being formed from different materials or various thicknesses, than the SCD 308 in one or more embodiments. In this manner, the SAVE graft's 136 sensitivity to pressure at the arterial end 320, the venous end 324, or both may be configured. For example, in one embodiment, the VPCS 332 may be formed from highly flexible material making the SAVE graft 136 more sensitive to venous pressure. In some embodiments, the APCS 316 may be formed from relatively rigid material to make the SAVE graft 136 less sensitive to arterial pressure.

As shown in FIG. 3, the SAVE graft 136 has a tapered or conical shaped APCS 316 and VPCS 332. This shape is beneficial as it provides a smooth slope towards the narrower SCD 308 in which blood may flow. In addition, the tapered shape helps direct pressure within the pressure reservoir 328 to the SCD 308 causing the SCD to collapse when appropriate. Of course, other shapes may be used. For example, the APCS 316, VPCS 332, or both may be square, rounded, rectangular, or other shapes.

Also as shown, the VPCS 332 has a larger volume than the APCS 316. This is beneficial in that it allows the VPCS 332 to exert more pressure on the pressure reservoir 328. In this manner, the SAVE graft 136 may be configured to be more sensitive to venous pressure. It is contemplated that the VPCS 332, APCS 316, or both may have different sizes. For example, they may be substantially equal in size, or the APCS 316 may be larger than the VPCS 332. This allows the SAVE graft 136 to be configured for various blood pressures allowing the graft to be used at various locations in a patient's body.

It is noted that the APCS 316 and VPCS 332 may be the same length in one or more embodiments, or have different lengths. Different lengths allow the SAVE graft 136 to respond differently to changes in arterial and venous pressure. For this reason, it is also contemplated that the SCD 308 may be longer than the APCS 316 and VPCS 332 in one or more embodiments.

As can be seen from the above, the SAVE graft 136 provides self regulation of blood pressure on both sides of the graft. The material and design dimensions of the SAVE graft 136 reduce the venous outflow to physiologic or natural levels while maintaining the required arterial pressure.

In some embodiments, an outer housing unit or puncture prevention guard (PPG) 336 may be included. The PPG 336 provides various benefits. The PPG 336 may be used to prevent the dialysis staff or other individual or event from inversely puncturing the inner components of the SAVE graft 136. The PPG 336 may also act as a reinforcing covering to prevent pressurization of the pressure reservoir 328 from expanding the outer wall 340 of the SAVE graft.

In some embodiments, the PPG 336 may be configured to allow outward expansion of the pressure reservoir 328, such as for the purpose of allowing a balloon angioplasty to be performed. As can be seen, the space between the PPG 336 and the outer wall 340 of the graft allows for expansion of the pressure reservoir 328. To illustrate, if the SAVE graft 136 were to stop flowing, clot intervention would be needed to clear the graft. Intervention of this type often requires balloon angioplasty. If needed, the SAVE graft 336 may be constructed so that a balloon can be fully expanded within the graft. When dilated with a balloon, the outer wall 340 will expand into the space provided by the PPG thus sparing the graft from damage.

As stated above, the SAVE graft 136 may be configured differently in various embodiments. For example, the internal conduit of a SAVE graft 136 need not form a pressure reservoir in all embodiments. It is contemplated that the collapsible portion of the internal conduit may contract (i.e., collapse) and expand from blood pressure of a surrounding blood flow as will be described below.

Figure 5A:
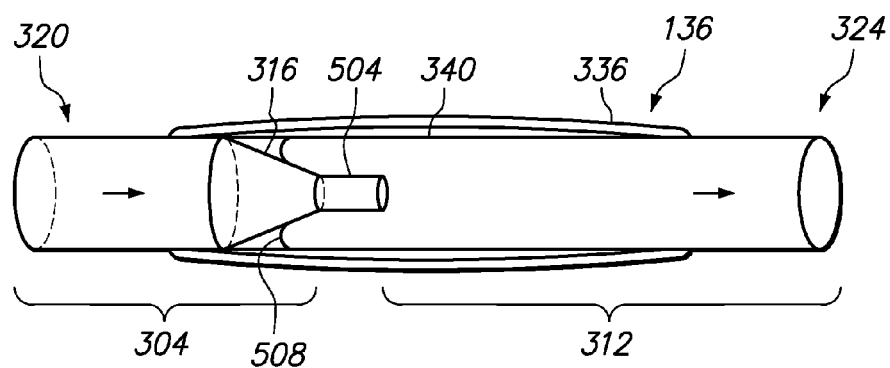
FIG. 5A is a cross section view illustrating an exemplary SAVE graft.

To illustrate, as shown in the embodiment of FIG. 5A, the SAVE graft 136 may have an open venous portion 312. In this embodiment, the VPCS and pressure reservoir may not be required and thus may not be included as part of the SAVE graft 136. This creates an open configuration that allows the venous pressure to act directly upon a venous controlled pressure nozzle (VCPN) 504 determining the luminal diameter and thus self regulating the stenosis provided by the SAVE graft 136. As will be described further below, the direct action of the venous pressure on the VCPN 504 allows the stenosis provided by the VCPN to be self regulated without the use of a pressure reservoir. Like the above embodiments, in this embodiment, the inflow end 320 may accept blood flow from an artery while the outflow end 324 allows blood to return to a patient through a vein.

Like the SCD of the above embodiments, a VCPN 504 may be a collapsible portion of the SAVE graft's internal conduit in one or more embodiments. The VCPN 504 may be formed from resilient flexible material such as described above with regard to other flexible or stretchable parts of the SAVE graft 136. In one embodiment, the VCPN 504 is cylindrical in shape. Of course other shapes may be used. For example, the VCPN 504 may be rectangular or square, include a taper, or be a combination thereof. A taper may be beneficial in that a taper may be more responsive to changes in pressure than a non-tapered shape.

Figure 5B:
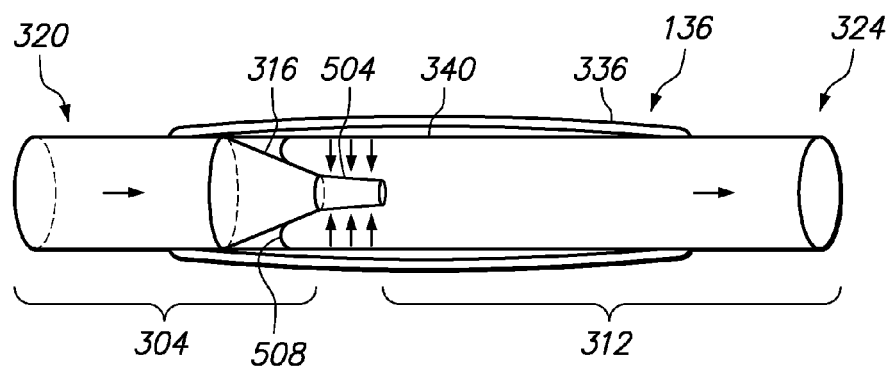
FIG. 5B is a cross section view illustrating an exemplary SAVE graft in an increased pressure state.

As shown by the arrows in FIG. 5B, during times of increased or high venous pressure the forces exerted by the pressure acts directly on a VCPN 504 to narrow the inner luminal diameter of the SAVE graft 136 thus restricting blood flow. At low venous pressure the VCPN 504 expands which expands the inner luminal diameter and allows increased blood flow. This is possible with a compliant VCPN 504 which expands or contracts based on the forces exerted by venous pressure.

In open configurations, clot prevention barriers 508 may be provided to prevent blood from pooling and clotting within the SAVE graft 136. In one or more embodiments, clot prevention barriers 508 prevent clotting by not allowing blood to reaching crevices or other areas within a SAVE graft 136 where the blood may become stagnant or pool. For example, a clot prevention barrier 508 may have a rounded shape to encourage blood flow to prevent pooling and clotting.

It is noted that in the above embodiments having a VPCS 332 (such as illustrated in FIG. 3), blood is channeled through the VPCS avoiding most if not all clot prone crevices or areas within a SAVE graft. In an open configuration, such as that of FIGS. 5A and 5B, it can be seen that without clot prevention barriers 508, blood may reach clot prone areas such as the area between the APCS 316 and the outer wall 304 of the SAVE graft. For this reason, clot prevention barriers 508 are advantageous in SAVE grafts 136 having an open configuration. Of course, clot prevention barriers 508 may also benefit other configurations of SAVE grafts 136 where there are areas prone to clotting.

To illustrate, in FIG. 5A, a clot prevention barrier 508 prevents blood from reaching an angled crevice between the outer wall 304 and the APCS 316 where it may clot. It is contemplated that one or more clot prevention barriers 508 may be used in other locations or embodiments of a SAVE graft as well. For example, in embodiments with a VPCS, a clot prevention barrier may be located around the VPCS to prevent blood from reaching a crevice formed between the VPCS and the outer wall of a SAVE graft (as can be seen in FIG. 3). Of course, clot prevention barriers 508 may not be required where there is little of no risk of clotting. It is noted that the materials used to form a clot prevention barrier 508 or other element of a SAVE graft 136 may include one or more anticoagulants to reduce the risk of clotting.

As can be seen, the SAVE graft provides a stenosis which is self regulating. As stated above, this is advantageous in that the stenosis does not have to be adjusted by an operator or physician. In this way, the SAVE graft is not susceptible to operator error the way other stenosis grafts are. The self regulating stenosis also self regulates for changes in a patient's blood pressure even if these changes are for a short period of time. A fixed stenosis does not provide this capability. In addition, an operator adjusted stenosis can only adjust through an operator's actions. Thus, small changes in blood pressure or changes in blood pressure which are not of sufficient duration to be detected by an operator may not be adjusted for.

The self regulated stenosis created by a SAVE graft provides the desired hemodynamic effects needed to improve dialysis and prevent many of the major problems associated with dialysis. For instance, a SAVE graft decreases the recirculation rates (non-dialyzed blood mixing with dialyzed blood) improving dialysis efficiency.

In addition, the SAVE graft allows normalization of the venous outflow pressures. Normally veins are low pressure systems. In a patient with a dialysis graft the large conduit attached to the artery transports blood with high flow and pressures into the graft and out though the patient's native veins. The native veins however cannot accommodate this high flow and pressure and eventually scar and shut down which is typically known as graft failure. The stenosis within the SAVE graft causes resistance to dampen this flow and pressure. In this manner, the stenosis creates an environment which is natural to the patient's circulatory system.

The SAVE graft also provides increased proximal arterial pressures. As stated above, the stenosis provided by the SAVE graft maintains the pressure at the arterial end preventing a steal syndrome which takes blood from the artery which can lead to limb loss or damage.

Another benefit of a SAVE graft is a reduction in loss of cardiac output. The resistance created by the stenosis of the SAVE graft creates resistance to flow which decreases loss of cardiac output. With the dialysis grafts and fistulas, high pressure and flow continuously course through the graft. Blood flow from the heart goes through the graft and then returns back to the lungs and heart without perfusing any tissue. This wastes the heart motion and puts excess strain on the heart through the patient's life.

Figure 6:
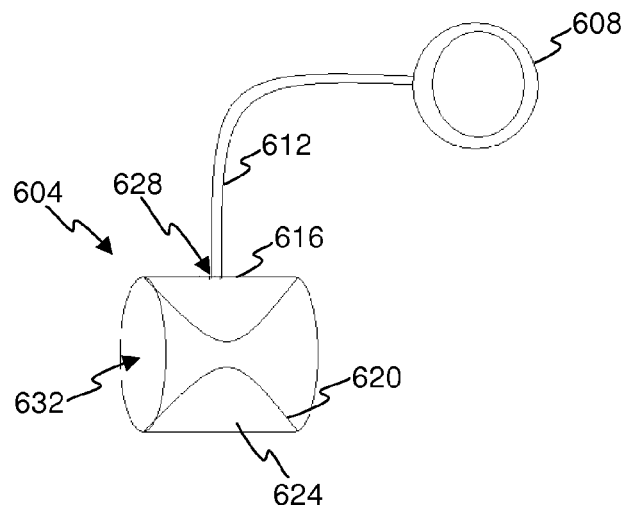
FIG. 6 is a side view illustrating an exemplary stenosis attachment.

Having described benefits of providing a stenosis above with regard to the SAVE graft, it is also contemplated herein that a stenosis may be provided in various other ways. For instance, FIG. 6 illustrates a stenosis attachment 604 which may be placed around an AVG or other graft to allow such graft to provide a stenosis. In other words, the stenosis attachment 604 may be used to retrofit existing grafts so that they may provide a stenosis.

In one or more embodiments, the stenosis attachment 604 may comprise an inner wall 620 and an outer wall 616. The outer wall 620 and inner wall 616 may be tubular in shape which provides an opening 632 to accept an AVG or other graft. Typically, the outer wall 620 and inner wall 616 will have a circular cross sectional shape, such as shown in FIG. 6, to allow the stenosis attachment 604 to accept a portion of a cylindrical AVG or other graft, as will be described further below. Of course other cross sectional shapes may be used.

The outer wall 620 and inner wall 616 may be sealed to one another to form a pocket 624. In the embodiment shown for example, the outer wall 620 and inner wall 616 are sealed together at their edges. The seal may be formed in various ways, now known or later developed. For example, the seal may be formed by one or more adhesives, welds, crimps, or a combination thereof. Of course, a seal may also be formed when the outer wall 620 and inner wall 616 are integrally formed.

Typically, the pocket 624 will be configured to retain a filler material, such as a fluid or a gas, without allowing such material to leak from the pocket. In this manner, the pocket 624 may be "inflated" or expand as it is filled with the filler material. Generally, the pocket 624 will be configured to expand inward to create a stenosis. This may be accomplished in various ways.

In one embodiment, the inner wall 620 may be formed from flexible and/or expandable material. This material may also be resilient to allow it to recover its shape. The outer wall 616 may be formed from a more rigid material. In this manner, as the pocket 624 is inflated with filler material, the flexible inner wall 620 may expand inward while the outer wall 616 generally retains its shape. As can be seen in FIG. 6, the inner wall 620 expands inward as the pocket 624 is filled with filler material.

An injection reservoir 608 may be provided to inflate and deflate (i.e. fill and empty) the pocket 624 in one or more embodiments. This allows the amount of stenosis provided by the stenosis attachment to be controlled. For this reason, it is contemplated that the injection reservoir 608 may be external to a patient's body in one or more embodiments.

The injection reservoir 608 may be configured to move filler material to the pocket 624 to inflate the pocket. This causes the inner wall 620 to expand inward which narrowing a stenosis provided by the stenosis attachment 604. In addition, the injection reservoir 608 may also remove or release filler material from the pocket 624 to deflate the pocket. This causes the inner wall 620 to return to an un-expanded state thereby decreasing the narrowing provided by the stenosis attachment 604. It is noted that the resiliency of the inner wall 620 allows the inner wall and thus the pocket 624 to automatically return to an un-expanded state when the filler material is removed or released from the pocket.

As can be seen, the injection reservoir 608 may be connected to the pocket 624 by a conduit 612 which allows filler material to flow between the injection reservoir and the pocket. The conduit 612 may be a tubular structure with a first end attached to the injection reservoir 608 and a second end attached to the pocket 624 to allow this flow of filler material. The conduit 612 may attach to an opening 628 in the outer wall 616 of the stenosis attachment 604 to allow filler material to flow into and out of the pocket via the conduit.

The injection reservoir 608 may function in various ways. For example, the injection reservoir 608 may comprise a pump which pumps filler material from into the pocket 624 through the conduit 612. The injection reservoir 608, conduit 612, or both may include a release valve which prevents filler material from escaping the pocket 624 unless deflation of the pocket is desired. When activated, the release valve may allow filler material to flow out of the opening 628 and back towards the injection reservoir 608. It is contemplated that the filler material may be stored in the injection reservoir 608 so that it may be later used to fill the pocket 624 again.

Figure 7:
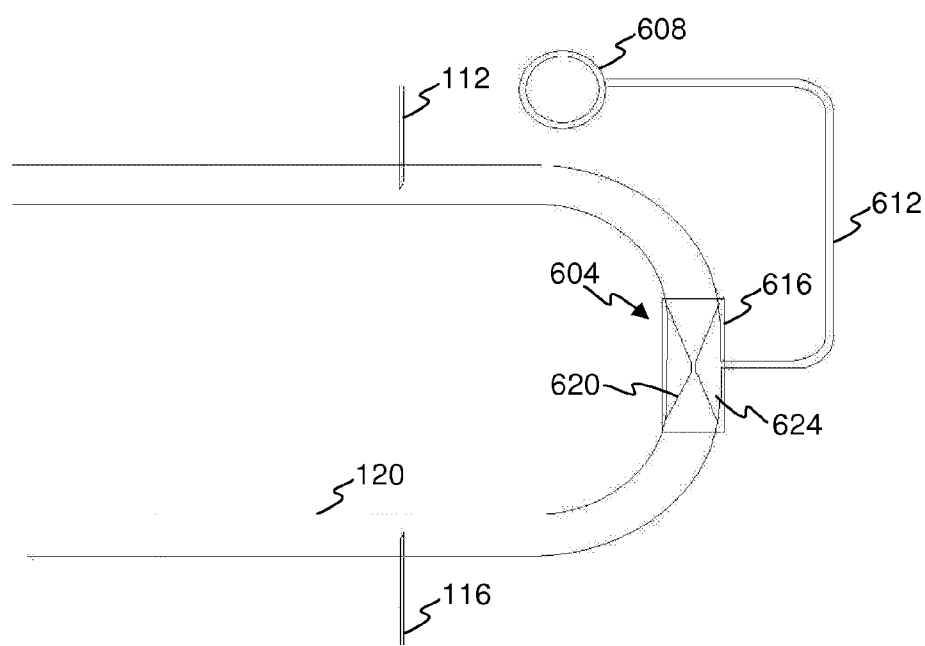
FIG. 7 is a side view illustrating an exemplary stenosis attachment on a graft.

FIG. 7 illustrates a stenosis attachment 604 placed on an AVG graft 120. Like the SAVE graft, the stenosis attachment 604 may be placed at the apex of the graft 120, or at other locations along the graft. In addition, the stenosis attachment 604 may be used with various types of grafts where a stenosis would be beneficial. For example, the stenosis attachment 604 may provide a stenosis for an AVG graft 120 or other graft used to provide access to blood flow for dialysis (or other procedures) via an inflow tube 116 and an outflow tube 112. As can be seen, the stenosis attachment 604 provides a stenosis for the graft 120 which ordinarily would not provide a stenosis. In this manner, a standard AVG graft 120 or other graft may be enhanced with the benefits of a stenosis.

The injection reservoir 608 may be operated to inflate or deflate the pocket 624 of the stenosis attachment 604. This causes the inner wall 620 of the stenosis attachment 604 to move inward which presses upon the AVG graft 120. As can be seen, the force of the inner wall 620 presses or pinches the AVG graft 120 narrowing its diameter where the inner wall contacts the graft. This provides a stenosis through the AVG graft 120. Deflating the pocket 624 causes the inner wall 620 to return towards the outer wall 616 and allows the AVG graft 120 to return to its normal diameter as well. It will be understood that the pocket 624 may be inflated various amounts to control or adjust the stenosis or narrowing provided by the stenosis attachment 604 and AVG graft 120.

The stenosis attachment 604 may be installed on an AVG graft 120 or other graft before or after the graft is implanted in a patient. Generally, this occurs by inserting the AVG graft 120 through the opening 632 of the stenosis attachment 604 such as shown in FIG. 6. The stenosis attachment 604 may be slid or moved along the AVG graft 120 to a desired position. As shown in FIG. 7 for example, the stenosis attachment 604 has been moved to the apex of the AVG graft 120.

Where the AVG graft 120 is already in a patient, the stenosis attachment 604 may be installed by disconnecting one end of the graft to allow the end of the graft to be inserted into the opening of the stenosis attachment. The stenosis attachment 604 may then be positioned along the AVG graft 120 as desired. The disconnected end of the AVG graft 120 may then reattached to an artery or vein to allow blood flow to resume through the graft.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A self adjusting graft comprising:
    an inflow end for accepting a blood flow from a circulatory system;
    an outflow end for returning the blood flow at an outflow pressure to the circulatory system;
    a conduit, having a fixed length, within the self adjusting graft configured to provide a fluid pathway for the blood flow between the inflow end and the outflow end;
    a sealed internal reservoir between the inflow end and the outflow end and having a reservoir pressure, the internal reservoir formed by an outer wall of the self adjusting graft and the conduit; and
    a collapsible portion of the conduit, the collapsible portion configured to provide a stenosis for the blood flow, wherein the outflow pressure increasing, caused by increasing blood pressure at the outflow end, relative to the reservoir pressure increases pressure in the internal reservoir which provides pressure on the collapsible portion to collapse the collapsible portion, and the outflow pressure decreasing relative to the reservoir pressure un-collapses the collapsible portion, wherein the collapsing the collapsible portion occurs without adding additional material to the reservoir and the graft is configured to be completely contained within a patient's body.

2. The self adjusting graft of claim 1, wherein the conduit comprises an expandable portion between the collapsible portion and the outflow end, the expandable portion configured to pressurize the internal reservoir by expanding into the internal reservoir as outflow pressure increases.

3. The self adjusting graft of claim 1, wherein the conduit comprises a tapered portion between the inflow end and the collapsible portion, the tapered portion configured to direct pressure within the internal reservoir to the collapsible portion to thereby collapse the collapsible portion.

4. The self adjusting graft of claim 1, wherein the conduit comprises a tapered portion between the inflow end and the collapsible portion and an expandable portion between the collapsible portion and the outflow end, such that:
    the expandable portion is configured to pressurize the internal reservoir by expanding into the internal reservoir as blood pressure at the outflow end increases; and
    a tapered portion configured to direct pressure within the internal reservoir on the collapsible portion to thereby collapse the collapsible portion.

5. The self adjusting graft of claim 1, wherein the collapsible portion has a cylindrical shape.

6. The self adjusting graft of claim 1, wherein the inflow end is configured to attach to an artery of the circulatory system and the outflow end is configured to attach to a vein of the circulatory system.

7. The self adjusting graft of claim 1 further comprising a puncture prevention covering surrounding at least a portion of the outer wall.

8. A method of controlling stenosis through a graft that is placed within a patient comprising:
    accepting a blood flow via a first end of a blood flow conduit within the graft, the blood flow conduit providing a fluid pathway within the graft for the blood flow;
    providing a collapsible portion of the blood flow conduit to form a stenosis;
    providing a pressure reservoir between an outer wall of the graft and the blood flow conduit;
    returning the blood flow to a circulatory system via a second end of the blood flow conduit;
    expanding, without the addition of material to the pressure reservoir, an expandable portion of the blood flow conduit as a result of increased blood pressure at the second end of the blood flow conduit, wherein the expandable portion expands into the pressure reservoir to increase pressure in the pressure reservoir; and
    collapsing the collapsible portion as a result of increased pressure within the pressure reservoir, wherein collapsing the collapsible portion narrows the stenosis.

9. The method of claim 8 further comprising directing pressure within the pressure reservoir toward the collapsible portion with a tapered portion of the blood flow conduit, wherein the tapered portion tapers inward toward the collapsible portion.

10. The method of claim 8 further comprising returning the expandable portion to an unexpanded state as the blood pressure at the second end of the blood flow conduit is reduced.

11. The method of claim 9 further comprising un-collapsing the collapsible portion as a result of decreased pressure within the pressure reservoir.

12. The method of claim 8 further comprising connecting an inflow end of the graft to an artery of the circulatory system and connecting an outflow end of the graft to a vein of the circulatory system.

13. The method of claim 8 further comprising increasing the rigidity of a portion of the outer wall of the graft with a reinforcing covering.

* * * * *